US007659078B1

(12) United States Patent
Daunert et al.

(10) Patent No.: US 7,659,078 B1
(45) Date of Patent: Feb. 9, 2010

(54) METHOD AND KIT FOR DETERMINATION OF PROSTACYCLIN IN PLASMA

(75) Inventors: Sylvia Daunert, Lexington, KY (US);
Michael Poon, New York, NY (US);
Urvee Desai, San Francisco, CA (US);
Sapna K. Deo, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 420 days.

(21) Appl. No.: 10/620,806

(22) Filed: Jul. 17, 2003

Related U.S. Application Data

(60) Provisional application No. 60/396,122, filed on Jul. 17, 2002.

(51) Int. Cl.
| G01N 33/53 | (2006.01) |
| G01N 33/537 | (2006.01) |
| G01N 33/543 | (2006.01) |
| G01N 33/88 | (2006.01) |
| C12Q 1/66 | (2006.01) |
| C07K 16/18 | (2006.01) |
| C07K 16/26 | (2006.01) |

(52) U.S. Cl. .......................... 435/7.1; 435/7.93; 435/8; 435/25; 435/69.1; 435/971; 435/975; 436/518; 436/538; 436/172; 530/389.2; 530/807

(58) Field of Classification Search ................. 435/7.1, 435/7.5, 7.93, 8, 25, 69.1, 971, 975; 436/518, 436/538, 172; 530/389.2, 807
See application file for complete search history.

(56) References Cited

U.S. PATENT DOCUMENTS

| 4,604,364 | A | * | 8/1986 | Kosak ......................... 436/501 |
| 5,486,455 | A | * | 1/1996 | Stults ............................. 435/6 |
| 5,876,935 | A |   | 3/1999 | Pankratz et al. |
| 5,942,407 | A | * | 8/1999 | Liotta et al. .................... 435/28 |

OTHER PUBLICATIONS

Pradelles et al., 1985. Enzyme immunoassays of eicosanoids using acetylcholine esterase as label: an alternative to radioimmunoassay. Anal. Chem. 57: 1170-1173.*
Luke et al., 1992. Determination of prostaglandin metabolites in biological samples by competitive time-resolved fluoroimmunoassay. Journal Immunological Meth. 148: 217-223.*
Desai et al., 2002. Determination of prostacyclin in plasma through a bioluminescent immunoassay for 6-keto-prostaglandin F1alpha: implication of dosage in patients with primary pulmonary hypertension. Anal. Chem. 74: 3892-3898.*
Zatta, Paolo F., "A new bioluminescent assay for studies of protein G and protein A binding to IgG and IgM." Journal of Biochemical and Biophysical Methods, 32, 1996, pp. 7-13.
Schramm, Wilifired., et al. "Rapid Solid Phase Immunoassay for 6-keto Prostaglandin $F_{1\alpha}$ on Microplates." Clinical Chemistry, 36/3, 1990, pp. 509-514.
Tonai, Takeharu., et al. "Enzyme Immunoassay of 6-ketoprostaglandin $F_{1\alpha}$ in solid phase." Biochimica et Biophysica Acta, 836, 1985, pp. 335-343.
Fischer, C., et al. "Simultaneous Determination of 6-oxo-prostaglandin $F_{1\alpha}$ and 2,3-Dinor-6-oxo-prostaglandin $F_{1\alpha}$ in Biological Fluids by Stable Isotope Dilution and Negative Ion Chemical Ionization Mass Spectrometry." Biomedical mass Spectrometry, vol. 12, No. 8, 1985, pp. 399-405.
Maclouf, Jacques., et al. "125 I Derivatives of Prostaglandins: A Novel Approach in Prostoglandin Analysis by Radioimmunoassay." Biochimica et Biophysica Acta, 431, 1976, pp. 139-146.
Zenno, Shuhei., et al. "Bioluminescent Immunoassay Using a Fusion Protein of Protein A and the Photoprotein Aequorin," Biochemical and Biophysical Research Communications, vol. 171, No. 1, Aug. 31, 1990, pp. 169-174.
Galvan, Barbara., et al. "Bioluminescence Hybridization Assays Using Recombinant Aequorin. Application to the Detection of Prostate-Specific Antigen mRNA." Analytical Chemistry, vol. 68, No. 20, Oct. 15, 1996, pp. 3545-3550.
Stults, Nancy, L.., et al. "Use of recombinant Biotinylated Aequorin in Microtiter and Membrane-Based Assays: Purification of Recombinant Apoaequorin from *Escherichia coli.*" Biochemistry, 1992, vol. 31, pp. 1433-1442.
Ramanatha, Sridhar., et al. "Heterogeneous bioluminescence binding assay for an octapeptide using recombinant aequorin." Analytica Chimica Acta, 369, 1998, pp. 181-188.
Shimimura, Osamu. "A Short Story of Aequorin." The Biological Bulletin, vol. 189, No. 1, Aug. 1995, pp. 1-5.

(Continued)

*Primary Examiner*—Ann Y. Lam
*Assistant Examiner*—James L. Grun
(74) *Attorney, Agent, or Firm*—McDermott Will & Emery LLP (57) ABSTRACT

A solid-phase immunoassay for 6-keto-Prostaglandin $F_{1\alpha}$, the stable hydrolysis product of prostacyclin (Prostaglandin $I_2$) is disclosed. Prostacyclin, a potent vasodilator with anti-platelet and anti-proliferative properties is an effective treatment for primary pulmonary hypertension and pulmonary arterial hypertension associated with scleroderma and scleroderma-like syndrome. Levels of 6-keto-Prostaglandin $F_{1\alpha}$ can be directly correlated with levels of prostacyclin. Therefore, 6-keto-Prostaglandin $F_{1\alpha}$ has become the indicator of choice to measure prostacyclin levels. The single step immunoassay for 6-keto-Prostaglandin $F_{1\alpha}$ uses the bioluminescent protein, aequorin as a label. Analyte-label conjugates were constructed by linking the carboxyl group of 6-keto-Prostaglandin $F_{1\alpha}$ and lysine residues of aequorin by chemical conjugation methods. The binding properties of 6-keto-Prostaglandin $F_{1\alpha}$ towards its antibody and the bioluminescent properties of aequorin are retained in the conjugate. The concentration of 6-keto-Prostaglandin $F_{1\alpha}$ after extraction from plasma shows good correlation with the concentration of 6-keto-Prostaglandin $F_{1\alpha}$ obtained without prior extraction of the same plasma sample. The assay allows the measurement of 6-keto-Prostaglandin $F_{1\alpha}$ directly in plasma without any pre-treatment of the samples, which results in a much simpler method with a faster assay time.

5 Claims, 4 Drawing Sheets

OTHER PUBLICATIONS

Lewis, J.C., et al. "Bioluminescence and Secondary Structure Properties of Aequorin Mutants Produced for Site-Specific Conjugation and Immobilization." Bioconjugate Chem, 2000, vol. 11, No. 1, pp. 65-70.

Grabarek, Zenon., et al. "Zero-Length Crosslinking Procedure with the Use of Active Esters." Analytical Biochemistry, 185, 1990, pp. 131-135.

* cited by examiner

METHOD AND KIT FOR DETERMINATION OF PROSTACYCLIN IN PLASMA

RELATED APPLICATIONS

This application claims the benefit of provisional application 60/396,122, filed Jul. 17, 2002, which is incorporated herein in its entirety.

This invention was made with government support provided by The National Institutes of Health.

FIELD OF THE INVENTION

The invention relates generally to methods of determining the level of prostacyclin in plasma using the conjugates. More particularly, the invention relates to a single step immunoassay for detection of the level of 6-keto-prostaglandin $F_1$, which directly correlates to the level of prostacyclin in plasma.

BACKGROUND OF THE INVENTION

Primary Pulmonary Hypertension (PPH) is a rare disease of the pulmonary vasculature, resulting in abnormally high pressure in the pulmonary artery, right ventricular failure, and death. While the pathogenesis of PPH is not clearly understood, the increased pulmonary vascular resistance observed is attributed to three main factors: 1) vasoconstriction, 2) thickening of the vessel wall due to vascular remodeling, and 3) in situ thrombosis. (Archer, S., Rich, S. *Circulation* 2000, 102, 2781-2791; Rich, S. *Curr. Treat Options. Cardiovasc. Med.* 2000, 2, 135-140). There is no cure for PPH and the treatment options are limited. (Naeije, R., Vachiery, J. L. *Clin. Chest Med.* 2001, 22, 517-527). The survival rate is less than a year in patients presented with New York Heart Association Functional Class IV symptoms. Although lung transplantation is a possible treatment option, there are obvious drawbacks such as shortage of donor organs and chronic rejection as well as the possibility of infection. (Franke, U., Wiebe, K., Harringer, W., Franke, T., Wittwer, T., Wahlers, T., Haverich, A. *Eur. J. Cardiothorac. Surg.* 2000, 18, 447-452). Long term intravenous treatment with epoprostenol (also known as prostacyclin or $PGI_2$) has greatly increased the survival rate.

Prostacyclin or $PGI_2$ (Prostaglandin $I_2$) is a major cyclooxygenase metabolite of arachidonic acid, and is mainly produced by vascular endothelial cells. Prostacyclin is a prostaglandin, which occurs along with other eicosanoids like thromboxanes and leukotrienes. Prostacyclin is a potent vasodilator with platelet-inhibitory, anti-proliferative and fibrinolytic activities. (Moncada, S., Vane, J. R. *Pharmacological Rev.* 1979, 30).

The exact levels of prostacyclin in human plasma are unknown, however like most eicosanoids it occurs in very low amounts (pg/mL). Thromboxane $B_2$ (metabolite of thromboxane $A_2$, a vasoconstrictor) and its metabolites occur in very low amounts like 1-10 pg/mL in plasma. Leukotrienes generally function as vasoconstrictors and bronchoconstrictors and occur in varying amounts in plasma and urine. Leukotriene $B_4$ occurs between 50 pg/mL-50 ng/mL, leukotriene $E_4$ occurs between 80 pg/mL-1000 ng/mg of creatinine. Prostaglandin $F_{2\alpha}$ concentrations are found between 10 pg/mL-100 pg/mL, prostaglandin $D_2$ is generally found at 5 pg/mL-500 pg/mL, and prostaglandin $F_{1\alpha}$ occurs at 1 ng/mL-100 ng/mL.

Currently intravenous epoprostenol is indicated for the chronic treatment of primary pulmonary hypertension (PPH) in New York Heart Association (NYHA) functional Class III and Class IV patients who do not respond to conventional therapy. (Krishnan, U. *Indian J. Pediatr.* 2000, 67, 523-527; Nauser, T. D., Stites, S. W. *Am. Fam. Physician* 2001, 63, 1789-1798). There is no set dose of prostacyclin for PPH and the starting dose varies between 4-8 ng/kg/min. Following the initiation of intravenous prostacyclin, most patients require an automatic dose increase of 2 ng/kg/min every two weeks until the rate of administration reaches 20 ng/kg/min. Further dose increase of 0.5 to 1 ng/kg/min per week is needed only upon the return of symptoms. Common side effects of intravenous prostacyclin include flushing, muscle pain, and abdominal cramps and these symptoms are not necessarily dose dependent. Thus, a method to quantify and correlate the plasma levels of prostacyclin with the onset of the untoward side effects or functional improvement would be useful in determining the optimal level of plasma prostacyclin for an individual patient.

A method to quantify the plasma levels of prostacyclin would be useful in determining the optimal level of plasma prostacyclin for an individual patient. Prostacyclin is very unstable with a half-life of only 60 minutes in plasma and 2-3 minutes in buffer. The immediate and stable product of hydrolysis of prostacyclin, 6-Keto-Prostaglandin $F_{1\alpha}$ (6-keto-$PGF_{1\alpha}$), is quantifiable and can be used as a surrogate marker of the level of plasma prostacyclin. The detection method for prostacyclin or its breakdown product has to be extremely sensitive and accurate since either molecule is present in very low amounts (pg/mL) in the body. Moreover, the existing methods are time consuming mainly due to the necessity to extract 6-keto-$PGF_{1\alpha}$ from biological samples. (Schramm, W., Smith, R. H., Jackson, T. M., Craig, P. A., Grates, H. E., and Minton, L. L. *Clinical Chem.* 1990, 36, 509-514; Tonai T., Y., K., Yano, T., Hayashi, Y., Yamamoto, S., Yamashita, K., and Miyazaki, H. *Biochim. Biophys. Acta* 1985, 836, 335-343). Thus there is a need for a rapid and sensitive detection method for prostacyclin. The present invention provides a single-step, solid phase immunoassay for 6-keto-$PGF_{1\alpha}$ using the bioluminescent protein aequorin.

SUMMARY OF THE INVENTION

In one aspect of the invention there is provided an assay for determining amount of prostacyclin in a plasma sample comprising:

(1) providing a plasma sample on a surface coated with an anti-immunoglobulin antibody;

(2) incubating the plasma sample with an effective amount of an anti-6-keto-$PGF_{1\alpha}$ primary antibody, a secondary anti-6-keto-$PGF_{1\alpha}$ antibody and 6-keto-$PGF_{1\alpha}$-aequorin conjugate;

(3) removing any unbound primary antibody and 6-keto-$PGF_{1\alpha}$-aequorin conjugate following incubation; and (4) measuring and correlating light intensity of the plasma sample with amount of prostacylin within the plasma sample.

In a preferred embodiment of this aspect of the invention, the assay is performed in a microtiter format. Preferably, the secondary antibody is coated onto a surface and exposed to the plasma sample, primary antibody and 6-keto-$PGF_1$-aequorin conjugate.

In another aspect of the invention there is provided a method of determining an appropriate dose of prostaglandin for the treatment of primary pulmonary hypertension in a patient comprising (1) providing a plasma sample from the patient;

(2) incubating the plasma sample with an effective amount of anti-6-keto-$PGF_1$ primary antibody, a secondary anti-6-keto-$PGF_1$ antibody, a 6-keto-$PGF_1$-aequorin conjugate;

(3) removing any unbound primary antibody and conjugate from the plasma sample following incubation;

(4) measuring and correlating amount of detected 6-keto-$PGF_1$ with the appropriate dosage of prostaglandin for the patient.

In another aspect of the invention there is provide a kit for measuring amount of prostacyclin in plasma comprising (1) a 6-keto-$PGF_1$-aequorin conjugate;

(2) an anti-6-keto-$PGF_1$ primary antibody; and (3) a secondary anti-6-keto-$PGF_1$ primary antibody coated plate.

DETAILED DESCRIPTION OF THE INVENTION

Various types of detection methods have been reported in the literature for prostacyclin using its stable hydrolysis product, 6-keto-$PGF_{1\alpha}$, as a measure of prostacyclin levels. For example, the methods include radioimmunoassays, enzyme immunoassays, and detection using gas liquid chromatography-mass spectrometry (GLC-MS) or gas chromatography-selective ion monitoring (GC-SIM). (Tonai T., Y., K., Yano, T., Hayashi, Y., Yamamoto, S., Yamashita, K., and Miyazaki, H. *Biochim. Biophys. Acta* 1985, 836, 335-343; Fischer C, M. C. *Biomed. Mass Spectrom.* 1985, 12, 399404; and Maclouf, J., Pradel, M., Pradelles, P. and Dray, F. *Biochim. Biophys. Acta* 1976, 431, 139-146. Radioimmunoassay is a highly sensitive method but it has the disadvantages associated with the use of radioactivity. Moreover, all the immunoassays or chromatographic techniques reported for 6-keto-$PGF_{1\alpha}$, require extraction of 6-keto-$PGF_{1\alpha}$ from plasma or plasma samples making the process laborious and time consuming. (Tonai T., Y., K., Yano, T., Hayashi, Y., Yamamoto, S., Yamashita, K., and Miyazaki, H. *Biochim. Biophys. Acta* 1985, 836, 335-343; Fischer C, M. C. *Biomed. Mass Spectrom.* 1985, 12, 399-404; and Maclouf, J., Pradel, M., Pradelles, P. and Dray, F. *Biochim. Biophys. Acta* 1976, 431, 139-146.

In contrast, the present invention provides a sensitive bioluminescent immunoassay for 6-keto-$PGF_{1\alpha}$ where the plasma samples are analyzed directly without requiring the extraction of 6-keto-$PGF_{1\alpha}$ from plasma. This results in a simpler, faster method for detection of this analyte in plasma samples. The present assay for 6-keto-$PGF_{1\alpha}$ is preferably performed in a microtiter plate format using the photoprotein aequorin as the label. Colorimetric and fluorescent assays could possibly suffer from background interference limiting their use in direct plasma analysis. Aequorin, however, being a bioluminescent label has virtually no background associated with aequorin is a highly sensitive label.

Aequorin has proved to be a highly sensitive label in the development of binding assays for the determination of large and small biomolecules. (Zenno, S., Inouye, S. *Biochem. Biophys. Res. Commun.* 1990, 171, 169-174; Christopoulos, T. K., and Galvan, B. *Anal. Chem.* 1996, 68, 3545-3550; Zatta, P. F. *J. Biochem. Biophys. Methods* 1996, 32, 7-13; Stults, N. L., Stocks, N. F., Riviera H., Gray J., McCann R. O., O'Kane D., Cummings R. D., Cormier M. J., and Smith D. F. *Biochemistry* 1991, 31, 1433-1438). The bioluminescent protein aequorin is native to the jellyfish *Aequorea victoria*. Aequorin is a bioluminescent photoprotein that is composed of an apoprotein (apoaequorin, 189 amino acid residues), a chromophoric unit (coelenterazine) and molecular oxygen. Aequorin has three $Ca^{2+}$ binding sites. When $Ca^{2+}$ binds to aequorin, it undergoes a conformational change that results in the oxidation of coelenterazine to coelenteramide and this produces $CO_2$ and emits a flash of light at 469 nm. The bioluminescent signal produced by aequorin has virtually no background signal and the quantum efficiency is between 11-17.5%, allowing it to be detected down to attomole levels. (Stults, N. L., Stocks, N. F., Riviera H., Gray J., McCann R. O., O'Kane D., Cummings R. D., Cormier M. J., and Smith D. F. *Biochemistry* 1991, 31, 1433-1438; Ramanathan, S., Lewis, J. C., Kindy, M. S., and Daunert, S. *Anal. Chim. Acta.* 1998, 369, 181-189; Shimomura, O. *Biol. Bull.* 1995, 189, 1-5; Lewis, J. C., Lopez-Moya, J. J., and Daunert S. *Bioconjugate Chem.* 2000, 11, 65-70).

In the present invention a cysteine-free mutant of aequorin is preferred because it shows enhanced activity. Lewis, J. C., Lopez-Moya, J. J., and Daunert S. *Bioconjugate Chem.* 2000, 11, 65-70, incorporated herein in its entirety. However, any suitable aequorin may be used as a label in the present methods and kits. Recombinant aequorin may be produced and purified for use in the present assay for 6-keto-$PGF_{1\alpha}$. For example, the compound 6-keto-$PGF_{1\alpha}$ may be conjugated to pure aequorin by conventional covalent attachment to the free amine groups of the lysine residues in aequorin. Aequorin contains 15 lysine residues.

In developing the present assay, the effect of choosing different initial ratios of analyte to the apoprotein on the bioluminescence properties of the protein, and the binding ability of an anti-6-keto-$PGF_{1\alpha}$ antibody was investigated. Further, the effect of an antibody for 6-keto-$PGF_{1\alpha}$ on the luminescence signal was evaluated. Based on the results, the sensitive bioluminescent binding assay for 6-keto-$PGF_{1\alpha}$ described herein was developed. The assay was then further optimized for detection of the analyte in plasma. Several plasma samples from PPH patients were analyzed by using them directly in the assay without any extraction of 6-keto-$PGF_{1\alpha}$.

In the present method, the detection and quantification of 6-keto-$PGF_{1\alpha}$ directly in a plasma sample without extraction of the prostaglandin is achieved using a 6-keto-PGF$_1$ antibody and a 6-keto-PGF-aequorin conjugate. The plasma sample may be diluted, for example about 200-fold with an appropriate medium, such as deionized water, and an effective amount of antibody and prostaglandin-conjugate added. An effective amount of antibody to be used in the assay dependent upon the particular antibody used and is selected to such that the light intensity generated therewith is sufficient to measure a signal above background, while keeping the amount of available binding sites to a minimum. In general, when the amount of antibody is increased, the sensitivity of the assay is improved but the detection limit of the assay is compromised. When a more diluted amount of antibody is used, the dynamic range is narrowed and sensitivity is reduced.

The amount of 6-keto-PGF-aequorin conjugate used in the present assay depends upon the specific conjugate used and can readily be determined by one of skill in the art. In general, the concentration range of conjugate is about $0.1 \times 10^{-10}$ to about $9 \times 10^{-10}$, preferably about $1 \times 10^{-10}$.

In carrying out the present assay in a microtiter plate format, a plasma sample is obtained from a patient and applied to a surface, such as a surface of a microtiter plate, that has been precoated with a secondary antibody. An amount of anti-6-keto-PGF$_{1\alpha}$ primary antibody and anti-6-keto-PGF$_{1\alpha}$-aequorin conjugate is then added to the plasma sample and the mixture incubated in the dark for a period of time ranging from about 1 to about 3 hours, preferably about 2 hours at room temperature. The surface is then washed to remove unbound primary antibody and conjugate, and the light intensity is determined and correlated with the amount of 6-keto-PGF$_{1\alpha}$ present in the sample, which in turn directly correlates with the amount of prostacyclin in the sample.

The determination of amount of prostacyclin in a sample obtained from a patient may then be used to determine the appropriate dosage of prostglandin to administer to a patient being treated for PPH, for example.

It has been observed in the scientific literature that the drug, Viagra®, available from Pfizer Inc. is a potential candidate for therapy in patients suffering from PPH. Sayin et al., Can. J. Cardiol., 2002, 18(6):676-678. It has been demonstrated that Viagra® acts as an inhibitor of the enzyme, phosphodiesterase. Inhibition of this enzyme causes increase in levels of cGMP and cAMP, which control growth of the smooth muscle cell layer that surrounds pulmonary arterioles. Proliferation of these smooth muscle cells has been linked with PPH. Prostacylin also acts as a dilator of smooth muscle cells by increasing the levels of cyclic nucleotides. Furthermore, it has been found that phosphodiesterase inhibitor enhances vasodilatory efficacy of prostacylin. Thus, the effects of Viagra® therapy on levels of prostacyclin in the blood can be determined using the assay for 6-keto-prostaglandin, described herein. Also, the appropriate dosage of Viagra® can also be determined by application of the assay for 6-keto-prostaglandin, described herein.

The present invention also provides unique aequorin mutants that are suitable for conjugation to 6-keto protaglandin F$_1$ for use in the above-described assays or for conjugation to other biomolecules, such as those suspected of playing a pathologicaal role in PPH, e.g., endothelin, angiotensin II, vasopressin, and neurotransmitter. These mutant aequorins can be conjugated to the desired biomolecule to analyze the role of the biomolecule in PPH, to analyze the metabolism of the biomolecule, to determine any correlation of serum level with physiological effect, or for drug design, for example. Similarly, these conjugates can be used in assays to determine the effects of the conjugated biomolecule on drug therapy, for example Aequorin- or mutant aequorin-biomolecule conjugates prepared either through non-specific, site-specific or genetic conjugation can be used in the assays of the invention. Aequorin mutants which have a unique cysteine at amino acid residue 69, 70, 74 or 76 (described in the examples) have been developed. These amino acid residues are close to the substrate-binding site in aequorin and therefore, binding of antibody to an analyte attached at any of these sites yields a homogeneous change in bioluminescence. Such results were demonstrated with an aequorin-thyroxine conjugate, where the thyroxine is bound to the sulfhydryl of a unique cysteine at position 71 of the aequorin molecule.

The present invention also contemplates kits for measuring amount of prostacyclin in a plasma sample. Kits preferably contain a primary antibody for 6-keto-PGF$_{1\alpha}$ and a secondary antibody and a 6-keto-PGF$_{1\alpha}$-aequorin conjugate. Preferably, the conjugate is a cysteine-free mutant of aequorin conjugated to 6-keto-PGF$_{1\alpha}$. The kit may also include assay buffer, deionized water, and/or microtiter plates or other surfaces pre-coated with the secondary antibody or for coating with secondary antibody at the time of performing the assay.

EXAMPLE 1

Reagents used in the examples herein include: Luria Bertani (LB) broth and agar were purchased from DIFCO Laboratories (Detroit, Mich.). Sodium dodecyl sulfate (SDS), sodium hydroxide, sodium chloride, calcium chloride, bovine plasma albumin (BSA), kanamycin, ethylenediaminetetra acetic acid (EDTA) disodium salt and 6-keto-Prostaglandin F$_{1\alpha}$ were obtained from Sigma Laboratories (St. Louis, Mo.). N-hydroxysuccinimide (NHS) and 1-Ethyl-3-(Dimethylaminopropyl) carbodiimide hydrochloride (EDC) were purchased from Pierce (Rockford, Ill.). HQH, quaternized polyethyleneimine anion exchanger was purchased from PerSeptive Biosystems (Cambridge, Mass.). The anti-6-keto-Prostaglandin F$_{1\alpha}$ antibody and the 96-well microtiter plates coated with anti-sheep-IgG were purchased from Assay Designs Inc. (Ann Arbor, Mich.). Tris (hydroxymethyl) amino methane (Tris) was purchased from Research Organics (Cleveland, Ohio). Coelenterazine was purchased from Biosynth International (Naperville, Ill.). Bradford assay kits were obtained from Bio-Rad Laboratories (Hercules, Calif.). Patient samples as well as control samples were provided by Dr. Michael Poon (Mount Sinai School of Medicine, N.Y.). All solutions were prepared using deionized (Milli-Q Water Purification System, Millipore, Bedford, Mass.) distilled water. All chemicals were analytical reagent grade or better, with >95% purity and were used as received.

Cell cultures were grown in an orbital shaker, Form a Scientific (Marrietta, Ohio) and centrifuged using a Beckman J2-MI centrifuge (Palo Alto, Calif.). The fractions were lyophilized using a VirTis Bench Top three freeze dryer (Gardiner, N.Y.). Bioluminescence measurements for the assay were made on MLX Microtiter Plate Luminometer Dynex (Chantilly, Va.). For all the measurements four replicates were performed and three of the closest were selected. All luminescence intensities reported are the average of three replicates, and have been corrected for the contribution of the background.

Expression and Purification of Apoaequorin: The plasmid pSD110 containing the cysteine free mutant (mutant S) of aequorin was constructed and initially transformed in competent B. subtilis cells. For protocols for the expression and purification of apoaequorin and the conversion of apoaequorin to the photoprotein, see Lewis, J. C., Lopez-Moya, J. J., and Daunert S. *Bioconjugate Chem.* 2000, 11, 65-70, incorporated herein.

Conjugation of Aequorin to 6-keto-Prostaglandin $F_{1\alpha}$: A volume of 1 mL of $1\times10^{-6}$ M. aequorin was allowed to incubate with coelenterazine for 3 h at 4° C. The N-hydroxysuccinimide ester of 6-keto-Prostaglandin $F_{1\alpha}$ was prepared by reacting with the water-soluble analog of N-hydroxysuccinimide (NHS), sulfo-NHS, and the dehydrating agent EDC. Grabarek. Z. a. G., J. *Anal. Biochem.* 1990, 185. The analyte 6-keto-Prostaglandin $F_{1\alpha}$ (1 mg/mL) was allowed to react with ~5 mM sulfo NHS and ~2 mM EDC (final concentrations) for 30 minutes at R.T. The reaction was quenched by adding β-mercaptoethanol to a final concentration of 20 mM. This NHS ester of the analyte was then conjugated to aequorin with bound coelenterazine in three different mole ratios, 1:50, 1:200, and 1:500 of aequorin: 6-keto-$PGF_{1\alpha}$ The conjugates were passed through a size exclusion column in order to remove any unconjugated NHS ester of 6-keto-$PGF_{1\alpha}$ and any residual reactants or reducing agent. The fractions were tested for activity of aequorin by taking 100 μL of each fraction, then adding 3 μL of $2.36\times10^{-4}$ M coelenterazine and measuring the intensity of light emitted as described before. The fractions showing activity were combined and lyophilized. The lyophilized conjugates were resuspended in 30 mM Tris-HCl buffer, pH 7.0, containing 2 mM EDTA, 0.15 M NaCl and 1 mg/mL BSA (assay buffer) and stored in aliquots at −80° C.

Calibration curves were generated for each of the conjugates (1:50, 1:200, 1:500) by first converting the apoaequorin conjugate to aequorin with coelenterazine as described before. Standard solutions were prepared by serially diluting the stock solutions of the conjugates assay buffer. A volume of 100 μL of these solutions was placed in a microtiter plate and the luminescence activity of aequorin was measured. The luminescence signal was integrated over a 3 second time period. All points were obtained in triplicates.

For the binder dilution studies aliquots of 100 μL of different concentrations of serially diluted anti-6-keto-$PGF_{1\alpha}$ antibody, produced in sheep and 50 μL of $1\times10^{-10}$ M 6-keto-$PGF_{1\alpha}$-aequorin conjugate were placed simultaneously in microtiter plates pre-coated with a secondary antibody, donkey anti-sheep IgG. All dilutions were done in the assay buffer. The plates were incubated in dark at room temperature for 2 h with shaking at 300 rpm. Then the plates were washed with wash buffer (30 mM Tris-HCL buffer, pH 7.0, containing 2 mM EDTA, 0.15 M NaCl, and 0.1% Tween 20) three times to remove any unbound primary antibody or any unbound conjugate. Finally, the light intensity was measured as described earlier for the calibration plot.

Dose-Response Curve: A dose-response curve was generated for 6-keto-$PGF_{1\alpha}$ by simultaneously incubating 100 μL of 6-keto-$PGF_{1\alpha}$ antibody (1:10,000 dilution), 50 μL of different concentrations of the serially diluted analyte, 6-keto-$PGF_{1\alpha}$, and 50 μL of $1\times10^{-10}$ M coelenterazine bound 6-keto-$PGF_{1\alpha}$-aequorin conjugate (1:500) on microtiter plates coated with the secondary antibody. The plate was incubated in dark at room temperature for two hours with shaking at 300 rpm. The plate was washed three times with the wash buffer to remove any unbound components. The light intensity was measured as described before.

A dose-response curve for 6-keto-$PGF_{1\alpha}$ in plasma was generated by preparing serially diluted standard solutions of 6-keto-$PGF_{1\alpha}$ in human plasma (previously diluted 1:200 times with deionized water) and adding them simultaneously with 6-keto-$PGF_{1\alpha}$-aequorin conjugate and the 6-keto-$PGF_{1\alpha}$ antibody to the wells with the immobilized secondary antibody. The incubation and washing steps were performed in the same manner as previously described in the generation of dose-response curve. The bioluminescence was triggered and measured as described before.

EXAMPLE 2

Construction of Plasmids containing Aequorin Mutants. The gene of a mutant apoaequorin in which all three cysteines of the native aequorin were replaced by serines was used as a template for the PCR. A unique mutation was introduced on the purified apoaequorin gene (Ala 69 to cysteine 69) by employing PCR site-directed mutagenesis. The oligonucleotides used for PCR are AQ69-1 and AQ69-2 (see Table 1). The following two primers were used as outside primers to introduce the restriction endonuclease site for Hind III and Sal I restriction enzymes:

1) TCTTCTTCTTCTTCTAAGCTTGTCAAGCTTACA-TCAGACTTCGACAACCCAAGA (SEQ ID NO. 1); and 2) AGAAGAAGMGAGTCGACCAGATCTGG-TACCCGGGAATT (SEQ ID No. 2).

The DNA obtained by PCR and the vector PFLAG-ATS which consists of the gene sequence for the octapeptide upstream of the multiple cloning site (MCS) were digested with the restriction enzymes Hind III and Sal I. Next, the digested DNA fragment was ligated into the plasmid pFLAG-ATS, to yield the pSD1004 vector. The apoaequorin mutants containing unique cysteine residues at position 70, 74 and 76 were prepared in the same manner (see Table 1) as described above. DNA sequencing was performed at the Macromolecular Center (University of Kentucky) to confirm the presence site-specific mutations.

Expression and Isolation of Aequorin Mutants. For expression of apoaequorin mutant 69 the plasmid pSD 1004 was transformed into Bacteria (*E. coli*, strain JM109). A 2 mL volume of LB broth containing 100 μg/mL of ampicillin was inoculated with a colony of bacteria containing plasmid pSD 1004. The cells were grown for 17 h at 37° C. in an aerated shaker. The cell culture was transferred to 400 mL LB broth containing 100 μg/mL ampicillin, and allowed to grow until it reached an absorbance of 0.6 at 600 nm. For induction of protein expression, 1 M IPTG stock solution was added such that the final IPTG concentration in the culture was 1.0 mM. The culture was allowed to grow for an additional 4.0 h at 37° C. in the shaker. The cells were centrifuged for 30 min at 27° C. and pelleted.

The apoaequorin mutant 69 thus expressed was released from the periplasm using an osmotic shock procedure. The pellets were first resuspended in 40 mL of 10 mM Tris-HCl/30 mM NaCl, pH 7.5. The cells were then collected by centrifuging for 15 min at 27° C., and were resuspended in 40 mL of 33 mM Tris-HCl, pH 7.5. The centrifugation and resuspension steps were repeated, but this time the cells were resuspended vigorously with 40 mL Stage I buffer. The resuspended cells were incubated at 37° C. for 10 min, with slow shaking. The cells were again collected by centrifuging for 10 min at 27° C. The pellets were finally resuspended rapidly with vigorous shaking for 10-15 min in 80 mL of chilled deionized-distilled water. After centrifuging for 10 min at 4° C., the supernatant was collected and lyophilized. The lyophilized sample was dissolved in deionized water and dialyzed three times against 30 mM Tris-HCl, pH 7.7, buffer containing 0.15 M sodium chloride, 2 mM EDTA, and 4 mM DTT. The dialyzed sample was then centrifuged for 10 min at 4° C. to remove any cell membrane fragments. The supernatant, which consisted of unpurified protein was filtered with a 0.2 μm syringe filter and was immediately purified. The apoaequorin mutants 70, 74 and 76 were expressed and isolated in the same way as described above by using bacteria containing plasmid pSD 1005, pSD 1006 and pSD 1007 respectively.

Purification of the Apoaequorin Mutants. The proteins were purified by using an anti-octapeptide M2 agarose affinity column. The column was equilibrated with 50 mM Tris-HCl, pH 7.4 containing 150 mM NaCl and 2 mM EDTA (TBS buffer). The solution containing protein was loaded on the column and the column was washed three times with 15 mL of TBS buffer. The proteins were eluted using 1 mL aliquots of 0.1 M glycine, pH 3.0, into tubes containing TBS buffer. The fractions containing the protein and their purity was determined by SDS-PAGE using 12.5% polyacrylamide gels, which were developed by silver staining (Pharmacia Biotech, Uppsala, Sweden). Fractions containing the fusion protein were pooled together and glucose was added to a final concentration of 30 mM followed by lyophilization. The lyophilized protein was resuspended in deionized distilled water. Excess salt was removed by dialyzing twice against 30 mM Tris-HCl, pH 7.4 containing 2 mM EDTA and 2 mM DTT. The protein concentration was determined by using the Bradford protein assay, with BSA as the standard.

Conversion of Apoaequorin Mutants to Photoproteins. A set amount of purified protein in 30 mM Tris-HCl, pH 7.4, buffer containing 2 mM EDTA and 2 mM DTT was mixed with a three time molar excess of coelenterazine in a glass tube. The mixture was briefly vortexed and then placed on ice for the required time.

Bioluminescence Emission Study. A volume of 10 μL of the mutant proteins at a concentration of 1 μg/mL was added to a glass tube, and the bioluminescence was measured by injecting 100 μL of luminescence triggering buffer (100 mM Tris-HCl, 100 mM $CaCl_2$, pH 7.5). The bioluminescence signal was collected at 0.1 second intervals over a 4 second time period.

Bioluminescence Emission Spectra of Apoaequorin Mutants. Luminescence was triggered by careful addition of 1.0 mL of a $1.0 \times 10^{-6}$ M solution of mutant aequorin using a constant-rate syringe pump into 0.5 mL of luminescence triggering buffer. Emission spectra were obtained using a Fluorolog-2 spectrofluorometer from Spex Industries (Edision, N.J.) without turning on lamp or chopper. The spectra were not corrected for changes in sensitivity of the photomultiplier tube to luminescence at different wavelengths.

Conjugation of Aequorin Mutant to Analyte: A volume of 1 mL of $1 \times 10^{-6}$ M. aequorin was allowed to incubate with coelenterazine for 3 h at 4° C. Five-fold excess of a maleimide/iodoacetamide derivative of analyte was allowed to react with mutant aequorin for 2 h at R.T. The conjugates were passed through a size exclusion column in order to remove any unconjugated maleimide/iodoacetamide derivative of analyte. The fractions were tested for activity of aequorin by taking 100 μL of each fraction, then adding 3 μL of $2.36 \times 10^{-4}$ M coelenterazine and measuring the intensity of light emitted as described before. The fractions showing activity were combined and lyophilized. The lyophilized conjugates were resuspended in 30 mM Tris-HCl buffer, pH 7.0, containing 2 mM EDTA, 0.15 M NaCl and 1 mg/mL BSA (assay buffer) and stored in aliquots at −80° C.

EXAMPLE 3

A comparative study between analysis of 6-keto-$PGF_{1\alpha}$ with and without extraction from plasma was carried out. In order to extract 6-keto-$PGF_{1\alpha}$ from plasma, a fixed volume of the plasma sample was first acidified with 2M HCl to pH 3.5. The sample was allowed to stand for 15 min at 4° C., after which it was centrifuged for 2 min to remove any precipitate. Meanwhile, a $C_{18}$-reverse phase column was washed with 10 mL ethanol, followed by 10 mL deionized water. The sample was then applied under a slight positive pressure to obtain a flow rate of 0.5 mL/min. The column was washed with 10 mL of water, followed by 10 mL of 15% ethanol and finally 10 mL of hexane. The sample was eluted using 10 mL of ethyl acetate. Elution was carried out at a flow rate of 2 mL/min. The ethyl acetate in the samples was evaporated under a stream of nitrogen. The dried samples were first dissolved in 50 μL ethanol, and then in the same volume of the assay buffer as that of the plasma sample initially used for extraction. These samples were used in the dose response curve performed in buffer.

The analysis of 6-keto-$PGF_{1\alpha}$ directly in plasma without extraction was performed by diluting the samples 1:200 times and using 50 μL in the dose-response curve along with 100 μL 6-keto-$PGF_{1\alpha}$ of antibody and 50 μL of 6-keto-$PGF_{1\alpha}$-aequorin conjugate. The analysis was performed in the same manner as the dose-response curve described before. The amount of 6-keto-$PGF_{1\alpha}$ in the samples was calculated from the standard dose response curve generated in plasma. The appropriate dilution factor was taken into consideration when calculating the amount of 6-keto-$PGF_{1\alpha}$ present in each sample.

For in vivo analysis plasma samples were obtained from five patients with severe pulmonary arterial hypertension and 7 normal controls. Written informed consent was obtained from all patients; the protocol was approved by the Institutional Review Board at Mount Sinai School of Medicine. Of the five patients, three were on chronic intravenous prostacyclin. All patient samples were analyzed in the same manner as the dose response curve in plasma. The samples were diluted 1:200 times to minimize matrix effects and 50 μL of the sample was used in the assay. The amount of 6-keto-$PGF_{1\alpha}$ in the samples was calculated as described before for sample analysis without extraction. All plasma samples were obtained and stored frozen at −20° C., in aliquots until use.

In order to obtain recovery data further analysis of the samples was performed. Two of the normal plasma samples and two patient plasma samples were first analyzed using the assay without extraction. Then the normal samples were spiked with 5 pg/mL of 6-keto-$PGF_{1\alpha}$ and the patient samples were spiked with 10 pg/mL of 6-keto-$PGF_{1\alpha}$ and the samples were used once again in the assay. In each case the samples were diluted 1:200 times to minimize matrix effects and 50 μL of the sample was used in the assay. The amount of 6-keto-$PGF_{1\alpha}$ in the samples was calculated as described before for sample analysis without extraction. The samples were analyzed in triplicates.

The plasmid containing the cysteine free mutant of aequorin was previously constructed in our laboratory. Lewis, J. C., Lopez-Moya, J. J., and Daunert S. *Bioconjugate Chem.* 2000, 11, 65-70. The cysteine free mutant of aequorin was chosen for the development of this assay because it showed enhanced activity as compared to wild-type aequorin. The cysteine free mutant of aequorin was expressed from plasmid pSD110. Purification of aequorin was carried out using an HQH anion exchange column. The fractions containing bioluminescence activity were lyophilized with glucose and later resuspended in deionized water. SDS-PAGE analysis was carried out to check the efficiency of purification. A single band was observed at ~20 kDa in the lyophilized fraction for pure aequorin. The yield of the protein was found to be 1.8 mg/L of culture.

Before conjugating 6-keto-PGF$_{1\alpha}$ to aequorin, the lyophilized fraction was dialyzed against bicarbonate buffer to remove any residual Tris-HCl salt, which might interfere with the conjugation. The dialyzed aequorin was then charged with 3 times molar excess of coelenterazine so that the analyte would not conjugate in the coelenterazine binding site, which might cause loss in activity of aequorin.

The conjugation method used involved a two-step coupling method using EDC (1-Ethyl-3-(Dimethylaminopropyl) carbodiimide hydrochloride) and sulfo NHS, which is a water soluble analog of NHS (N-hydroxy succinimide). EDC, a dehydrating agent, reacts with the carboxyl group of 6-keto-PGF$_{1\alpha}$, and forms an amine-reactive unstable, O-acylisourea-intermediate of 6-keto-PGF$_{1\alpha}$. NHS reacts with the O-acylisourea-intermediate to form an NHS ester to stabilize this intermediate. The NHS ester then reacts with the amine groups on aequorin. The advantage of the two-step procedure is the prevention of the modification of the protein carboxyl groups due to exposure to EDC. Grabarek, Z. a. G., J. *Anal. Biochem.* 1990, 185. The reaction is quenched by a thiol-containing compound like β-mercaptoethanol. Three different conjugates were prepared (1:50, 1:200, 1:500) using this method, by increasing the initial molar concentration of the NHS ester of 6-keto-PGF$_{1\alpha}$ while keeping the concentration of aequorin constant. The conjugates were passed through a size exclusion column to remove any unconjugated ester of 6-keto-PGF$_{1\alpha}$ and unreacted β-mercaptoethanol. They were then lyophilized and later resuspended in the assay buffer.

In order to study the effect of conjugation on the bioluminescence activity of aequorin and to select an appropriate conjugate concentration for the assay, calibration plots were constructed for each of the conjugates (data not shown). The conjugates (1:50, 1:200 and 1:500) could be detected down to $1\times10^{-12}$ M. A concentration of $1\times10^{-10}$ M of the three conjugates was selected for the binder dilution study. This concentration was low enough to be able to detect aequorin at low levels with high sensitivity and at the same time it showed much higher activity than the background.

Figure 1:
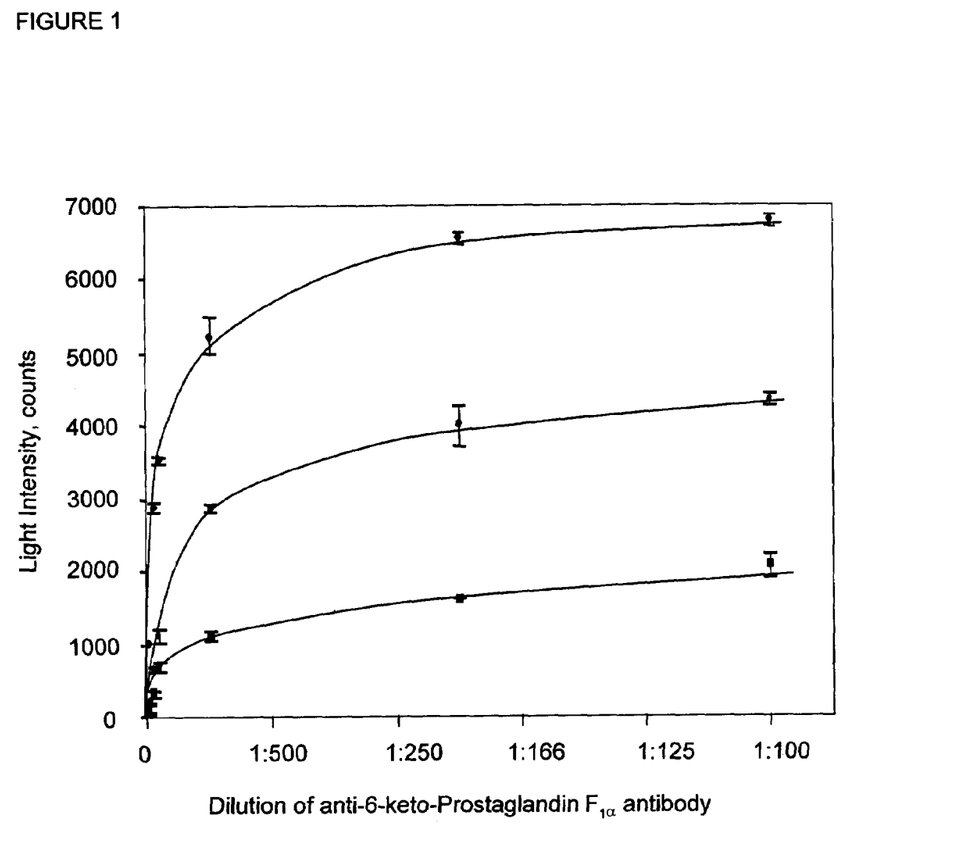
FIG. 1 shows the binder dilution curves obtained by incubating a volume of 100 µL of varying concentrations of 6-keto-$PGF_{1\alpha}$ antibody and 6-keto-$PGF_{1\alpha}$-aequorin conjugates with secondary antibody coated plates. Data are an average of three points±the standard deviation. (■) 1:50 Conjugate, (●) 1:100 Conjugate, (♦) 1:500 Conjugate.
Figure 2:
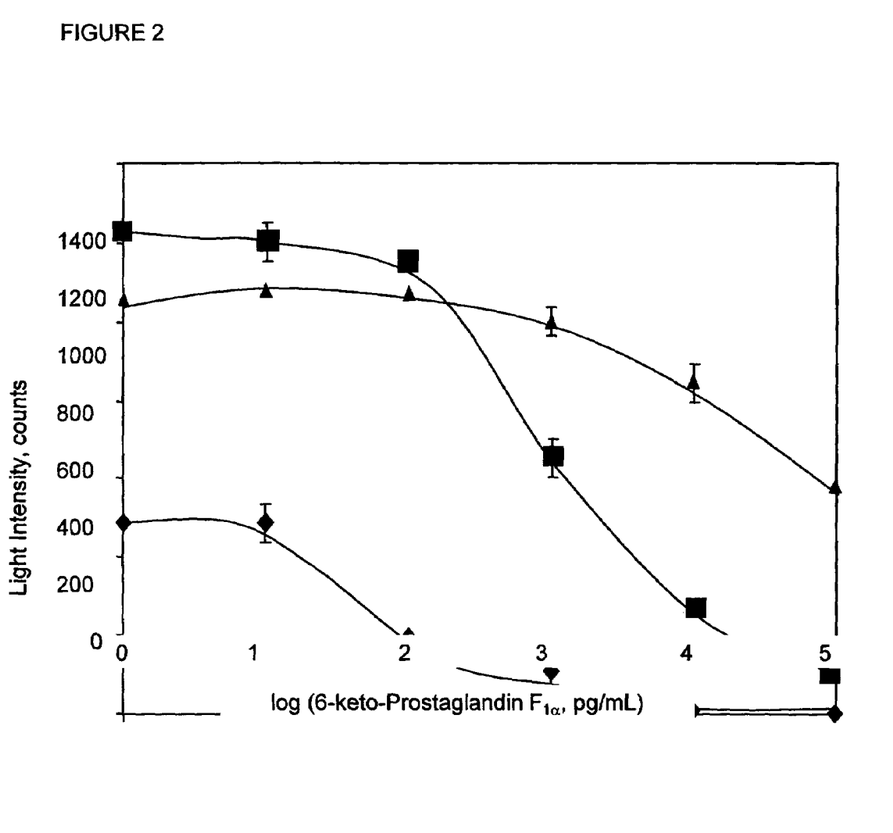
FIG. 2 shows the dose-response curves for 6-keto-$PGF_{1\alpha}$ generated by incubating varying concentrations of 6-keto-$PGF_{1\alpha}$ with $1\times10^{-10}$ M conjugate and (■) 1:5000 dilution of 6-keto-$PGF_{1\alpha}$ antibody, or (♦) 1:50,000 dilution of 6-keto-$PGF_{1\alpha}$ antibody and 1:10,000 dilution of 6-keto-$PGF_{1\alpha}$ antibody with ( )$1\times10^{-9}$ M 6-keto-$PGF_{1\alpha}$-AEQ conjugate. Data are an average of three points±the standard deviation.
Figure 3:
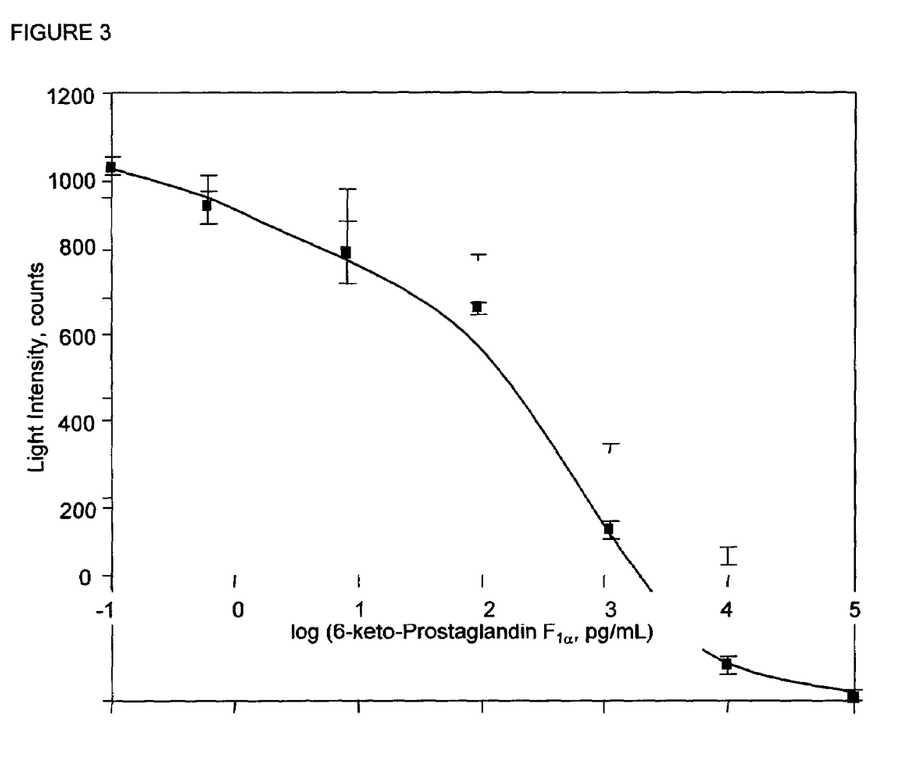
FIG. 3 is a dose-response curve for 6-keto-$PGF_{1\alpha}$ obtained by incubating 100 µL of 6-keto-$PGF_{1\alpha}$ antibody, 50 µL volume of $1\times10^{-10}$ M 6-keto-$PGF_{1\alpha}$-AEQ conjugate and varying concentrations of 6-keto-$PGF_{1\alpha}$. Data are an average of three points±the standard deviation.

The next step was to study the interaction between the anti-6-keto-PGF$_{1\alpha}$ antibody and the conjugates. For this, binder-dilution curves were generated for all three conjugates as shown in FIG. 1. The 6-keto-PGF$_{1\alpha}$ antibody was incubated with a concentration of $1\times10^{-10}$ M of the conjugates in the secondary antibody-coated microtiter plate for 2 h at room temperature. After washing the plate to remove any unbound antibody or conjugate the luminescence was measured. As the concentration of antibody increased the light intensity increased until it reached a concentration after which there was no significant increase. It was observed that the 1:500 conjugate showed maximum binding therefore, it was used for the remaining experiments in the assay. The amount of antibody to be used in the assay was selected such that the light intensity emitted is sufficient to measure a signal above the background, while keeping the amount of available binding sites to a minimum. The antibody dilution selected for developing the assay was 1:10,000 dilution. The effect of increased or decreased amounts of 6-keto-PGF$_{1\alpha}$ antibody and/or conjugate on the dose-response curve was also evaluated. In the first two cases, the conjugate concentration was kept constant at $1\times10^{-10}$ M, whereas the antibody concentration was either increased or decreased by a factor of 5. In the third experiment, the antibody concentration used was a 1:10,000 dilution, and the conjugate concentration was increased to $1\times10^{-9}$ M. As shown in FIG. 2, when a higher antibody concentration is used, the sensitivity improves but the detection limit is compromised. When a more diluted amount of antibody is used, the dynamic range narrows significantly and the sensitivity is reduced. Finally, when a higher concentration of the conjugate is employed both, the detection limit and the dynamic range worsen. Therefore, based on these data, the optimum antibody dilution for the assay was determined to be 1:10,000 and the conjugate concentration to be $1\times10^{-10}$ M (FIG. 2). Next, a dose-response curve was generated by simultaneously mixing varying concentrations of free 6-keto-PGF1α, $1\times10^{-10}$ M of the 1:500 conjugate, and 1:10,000 dilution of the 6-keto-PGF1α antibody and incubating them in microtiter plates immobilized with the secondary antibody. The dose-response curve obtained for 6-keto-PGF1α as depicted in FIG. 3, is sigmoidal in shape, with the luminescence intensity being lower at high concentrations of 6-keto-PGF1α and increasing as the concentration of 6-keto-PGF1α decreases. The working range of the curve ranges for concentrations of 10,000 pg/mL-1 pg/mL. The detection limit for 6-keto-PGF1α was determined to be 1 pg/mL, which corresponds to a $2\times10^{-12}$ M concentration of 6-keto-PGF1α.

Figure 4:
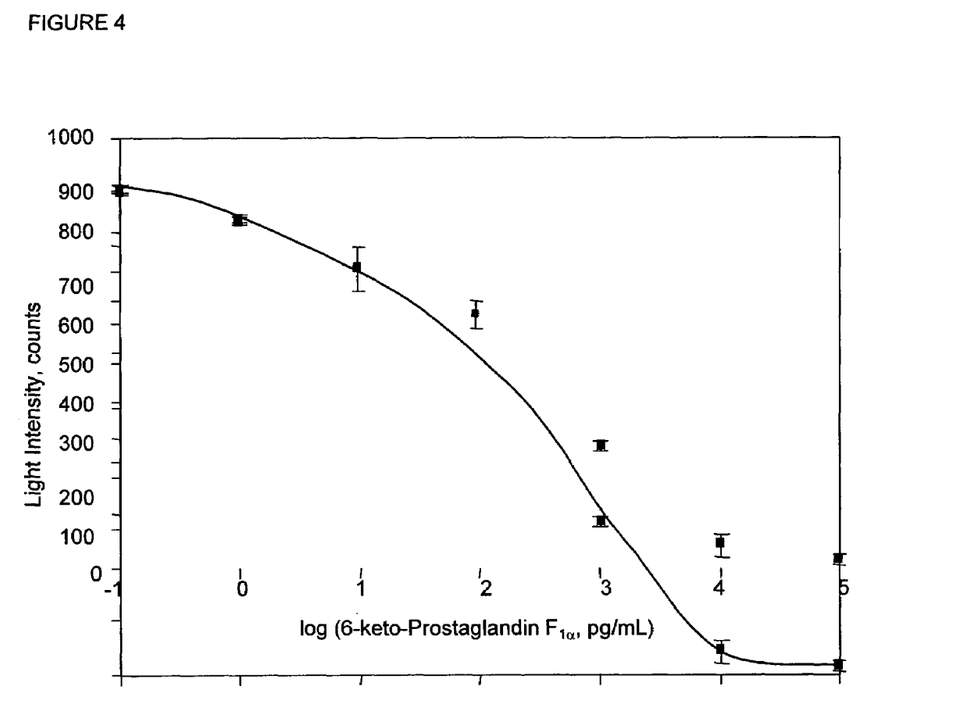
FIG. 4 is a dose-response curve for 6-keto-$PGF_{1\alpha}$ in plasma of a healthy person obtained by incubating 100 µL of 6-keto-$PGF_{1\alpha}$ antibody, 50 µL volume of $1\times10^{-10}$ M 6-keto-$PGF_{1\alpha}$-AEQ conjugate and varying concentrations of 6-keto-$PGF_{1\alpha}$ in 1:200 diluted plasma. Data are an average of three points±the standard deviation.

Since the goal was to detect 6-keto-PGF1α in plasma, it was necessary to validate this assay in plasma and to study any possible matrix effects on the performance of the conjugate or the binding capabilities of the 6-keto-PGF$_{1\alpha}$ antibody in plasma. The assay was, therefore, performed in 1:200 diluted human plasma spiked with known concentrations of 6-keto-PGF$_{1\alpha}$. The dose-response curve obtained (FIG. 4) was almost identical to that obtained for 6-keto-PGF$_{1\alpha}$ in buffer. According to this dose response curve, and as expected of 6-keto-PGF$_{1\alpha}$ at high concentrations of free 6-keto-PGF$_{1\alpha}$ most of the binding sites are occupied by 6-keto-PGF$_{1\alpha}$, and therefore, a low bioluminescence signal in the solid phase was obtained. As the concentration of free-analyte decreases, the bioluminescence intensity reaches a maximum since most of the binding sites on the antibody are occupied by the conjugate. The detection limit of this dose-response curve was also found to be 1 pg/mL and the limit of quantitation was found to be 5.11 pg/mL. This demonstrates that even low levels of 6-keto-PGF$_{1\alpha}$ could be detected in the assay, and also that aequorin is an excellent label for the detection of biomolecules in biological fluids.

The inter-assay precision was determined by generating the dose-response curve in plasma for five consecutive days in exactly the same manner as described earlier. The percent coefficient of variation for samples containing different concentrations of 6-keto-PGF$_{1\alpha}$, was calculated. The average coefficient of variation was found to be 4.5%. The intra-assay precision was determined by doing 4 replicate measurements of the same sample. The average coefficient of variation was found to be 1.25%.

Presence of various prostaglandins other than 6-keto-PGF$_{1\alpha}$ in the blood can cause non-specific binding with the 6-keto-PGF$_{1\alpha}$ antibody and interfere with the detection of 6-keto-PGF$_{1\alpha}$, giving extremely high values of 6-keto-PGF$_{1\alpha}$. Therefore, it becomes important to confirm that the amount of 6-keto-PGF$_{1\alpha}$ obtained from our assay is only due to 6-keto-PGF$_{1\alpha}$ and no other prostaglandin. The cross-reactivities of other prostaglandins similar in structure to 6-keto-PGF$_{1\alpha}$ were determined by preparing standard solutions of the compounds in the assay buffer ranging from 100,000 to 100 pg/mL and using them in this assay for 6-keto-PGF$_{1\alpha}$.

The measured 6-keto-PGF$_{1\alpha}$ concentration at 50% B/B$_0$ was then calculated. The percent cross-reactivities were calculated by comparison of measured cross-reactant concentration and the actual concentration (known amount) of the cross-reactant in the sample (Table 1). It must be noted that the prostaglandins occur at different times in the arachidonic acid pathway and in different concentrations. Also, 2,3-dinor-6-keto-Prostaglandin F$_{1\alpha}$ is found in urine and does not occur in plasma, however since it is the immediate metabolite of 6-keto-PGF$_{1\alpha}$ we decided to analyze the cross-reactivity of 2,3-dinor-6-keto-Prostaglandin F$_{1\alpha}$ as well. From the table it is clear that the prostaglandins do not show any significant amount of cross-reactivity. This indicates that the assay is specific only for 6-keto-PGF$_{1\alpha}$ and there is no interference from other prostaglandins, which might be present in the plasma samples. The assay can, therefore, be used to measure 6-keto-PGF$_{1\alpha}$ directly from plasma.

TABLE 1

| | Oligonucleotide sequence of primers | |
|---|---|---|
| AQ69-1 | GCCTTCTTCGGAGGATGTGGAATGAAATAT (SEQ ID NO. 3) | Ala69-Cys69 |
| AQ69-2 | ATATTTCATTCCACATCCTCCGAAGAAGGC (SEQ ID NO. 4) | Ala69-Cys69 |
| AQ70-1 | GCTTGCATGAAATATGGTGTGGAAACTGAT (SEQ ID NO. 5) | Gly70-Cys70 |
| AQ70-2 | ATCAGTTTCCACACCATATTTCATGCAAGC (SEQ ID NO.6) | Gly70-Cys70 |
| AQ74-1 | GCTGGAATGAAATATTGTGTGGAAACTGAT (SEQ ID NO. 7) | Gly74-Cys74 |
| AQ74-2 | ATCAGTTTCCACACAATATTTCATTCCAGC (SEQ ID NO. 8) | Gly74-Cys74 |
| AQ76-1 | ATGAAATATGGTGTGTGCACTGATTGGCCT (SEQ ID NO. 9) | Glu76-Cys76 |
| AQ76-2 | AGGCCAATCAGTGCACACACCATATTTCAT (SEQ ID NO. 10) | Glu76-Cys76 |

EXAMPLE 3

Cross-reactivities of related prostaglandins were measured by using varying concentrations of 50 μL of the cross reactant in the dose response curve instead of 6-keto-PGF$_{1\alpha}$. The percent cross-reactivities were calculated at 50% B/B$_0$. The results are shown in Table 2.

TABLE 2

| Analyte | Percent Bound | Average Standard Deviation |
|---|---|---|
| 6-keto-Prostaglandin F$_1$ | 100% | 1.71 |
| Prostaglandin F$_1$ | 5.4% | 4.65 |
| Prostaglandin F$_2$ | 3.41% | 3.21 |
| 13,14-dihydroxy-15-keto-Prostaglandin F$_1$ | 0.45% | 1.01 |
| 2,3-dinor-6-keto-Prostaglandin F$_1$ | 10.1% | 5.78 |
| Prostaglandin D$_2$ | 7.75% | 2.11 |
| Prostaglandin E$_1$ | 6.75% | 3.87 |
| 6,15-diketo-13,14-dihydro-Prostaglandin F$_1$ | 1.83% | 0.92 |

EXAMPLE 4

In vivo sample analysis was performed with the present assay. The PPH patients and control samples were provided by Dr. Michael Poon of the Mount Sinai Pulmonary Hypertension Program. Five PPH patient plasma samples were diluted (1:200) times with buffer and used directly in the assay. The concentration of 6-keto-PGF$_{1\alpha}$ in the samples was measured using the standard dose response curve obtained in plasma by diluting plasma of a normal subject (1:200) to measure the amount of 6-keto-PGF$_{1\alpha}$. It was observed that the levels of 6-keto-PGF$_{1\alpha}$ increased with increase in the prostacyclin dose. Three normal control samples were used to produce the standard dose-response curves, and the curves were found to be similar. The values of 6-keto-PGF$_{1\alpha}$ in the samples of patients obtained with each of the standard curves were also similar. Table 2 shows the 6-keto-PGF$_{1\alpha}$ values in normal and patients samples in vivo. Plasma samples of the normal subjects were used to produce standard dose-response curves and values of 6-keto-PGF$_{1\alpha}$ in patient samples were obtained using those curves. The measurements were performed in triplicates. The results are shown in Table 3.

TABLE 3

| Plasma Sample | Prostacyclin Dose (ng/kg/min) | 6-keto-Prostaglandin F$_1$ concentration measured without extraction (ng/ml) | Standard Deviation |
|---|---|---|---|
| Average of 3 normal samples | — | 1.7 | 0.01 |
| PPH Patient 1 | 28.5 | 9.9 | 0.2 |
| PPH Patient 2 | 10 | 6.7 | 0.05 |
| PPH Patient 3 | 8 | 4.1 | 3.1 |
| PPH Patient 4 | 0 | 2.2 | 1.5 |
| PPH Patient 5 | 0 | 1.5 | 0.05 |

EXAMPLE 5

In order to verify the concentration of 6-keto-PGF$_{1\alpha}$ obtained from plasma using the assay of the present invention, 6-keto-PGF$_{1\alpha}$ was extracted from the plasma samples of 7 normal subjects and the 5 PPH patients using the C$_{18}$-Sep-Pak columns, and these values were compared with the values obtained when plasma samples were used directly in our assay without extraction. In the extraction method, the 6-keto-PGF$_{1\alpha}$ was obtained in the ethyl acetate fraction. All ethyl acetate was evaporated under N$_2$ and the dried 6-keto-PGF$_{1\alpha}$ was dissolved first in ethanol followed by the assay buffer. This 6-keto-PGF$_{1\alpha}$ was used in the assay performed in buffer. The concentrations of 6-keto-PGF$_{1\alpha}$ obtained using the aequorin assay in plasma samples, without pretreatment were observed to be highly correlated with the measured 6-keto-PGF$_{1\alpha}$ after extraction. The equation for the straight line can be given as $y=0.79x+418$, $r=0.988$, $n=12$.

Further in vivo analysis was performed in order to determine the recovery of 6-keto-PGF$_{1\alpha}$ from samples using this assay. Two of the normal plasma samples and two patient plasma samples were first analyzed using the assay as described before and determining the concentration of 6-keto-PGF$_{1\alpha}$ present in the samples by using the standard curve in 1:200 diluted plasma. A known amount of 6-keto-PGF$_{1\alpha}$ was spiked into the samples and the samples were analyzed once again to determine the concentration of 6-keto-PGF$_{1\alpha}$. Percent recovery data were obtained using the concentration of 6-keto-PGF$_{1\alpha}$ in unspiked samples and the concentration obtained after spiking. It is clear from the data (Table 3) that this assay for 6-keto-PGF$_{1\alpha}$ gives recoveries within the range error. Percent recovery data of normal samples and patient samples are shown in Table 4. The measurements were performed in triplicate.

TABLE 4

| Subject | Prostacyclin Dose (ng/kg/min) | Weight (kg) | Concentration of 6-keto-PGF$_1$ found in unspiked samples (ng/ml) | Amount of 6-keto-PGF$_1$ spiked into samples (ng/ml) | Concentration of 6-keto-PGF$_1$ found in spiked samples (ng/ml) | Percent Recovery |
|---|---|---|---|---|---|---|
| Normal sample | 0 | — | 2.05 | 5 | 7.53 | 106.8% |
| Normal sample | 0 | — | 2.91 | 5 | 8.01 | 109% |
| PPH patient 1 | 10 | 95 | 8.32 | 10 | 20.2 | 115% |
| PPH patient 2 | 28.5 | 78.5 | 9.96 | 10 | 21.7 | 117.4% |

In conclusion, this immunoassay, is the first direct assaying technique for quantification of plasma 6-keto-PGF$_{1\alpha}$ without the process of extraction. The 6-keto-PGF$_{1\alpha}$ concentrations obtained from patient samples by extraction and without extraction show good correlation. In addition, the antibody employed for the assay, and hence the assay itself, does not show significant binding to other related prostaglandins. Therefore, the possibility of obtaining falsely high values of 6-keto-PGF$_{1\alpha}$ due to the presence of other similar prostaglandins is eliminated. The assay has a wide working range, and a low detection limit of 1 pg/mL, which enables the measurement of the creation of distribution curves of plasma prostacyclin levels in normal and disease states. This assay also characterizes the application of aequorin in quantification of important components present in the body by directly measuring them in the biological matrix without requiring any pre-treatment of the biological fluids. This assay may allow high throughput analysis of the levels of plasma prostacyclin in patients with primary pulmonary hypertension and the clinical implications of various levels of plasma prostacyclin in the pathogenesis and clinical management of this devastating disease.

The following abbreviations are used herein: 6-keto-PGF$_{1\alpha}$: 6-keto-ProstaglandinF$_{1\alpha}$; PPH: Primary Pulmonary Hypertension; EDC: 1-Ethyl-3-(Dimethylaminopropyl) carbodiimide hydrochloride; NHS: N-hydroxysuccinimide; BSA: Bovine plasma albumin; SDS-PAGE: Sodium dodecyl sulfate-Polyacrylamide gel electrophoresis; Tris: Tris (hydroxymethyl)amino methane; EDTA: ethylenediaminetetraacetic acid.

What is claimed is:

1. A method of determining amount of prostaglandin in a plasma sample comprising:
   (1) providing a plasma sample from a patient in contact with a surface coated with an anti-immunoglobulin antibody;
   (2) incubating the plasma sample with an effective amount of an anti-6-keto-prostaglandin $F_{1\alpha}$ (6-keto-$PGF_{1\alpha}$) antibody, wherein the anti-immunoglobulin antibody binds to the anti-6-keto-$PGF_{1\alpha}$-antibody, and with a conjugate comprising 6-keto-$PGF_{1\alpha}$ covalently bound to an aequorin mutant,
   wherein said aequorin mutant comprises serine substitutions for all three cysteine residues as present in wild-type aequorin (Cys→Ser), wherein said aequorin mutant further comprises a single cysteine residue substituted at amino acid position 69 (Ala69 →Cys), 70 (Gly70 →Cys), 74 (Gly74 →Cys) or 76 (Glu76 →Cys), and
   wherein the 6-keto-$PGF_{1\alpha}$ is coupled to the aequorin mutant via reaction with the sulfhydryl group of the single cysteine;
   (3) removing any unbound anti-6-keto-$PGF_{1\alpha}$-antibody and said conjugate following incubation;
   (4) measuring light intensity of the 6-keto-$PGF_{1\alpha}$ conjugate bound to the anti-immunoglobulin antibody; and
   (5) correlating the light intensity of the bound 6-keto-$PGF_{1\alpha}$ conjugate with the amount of the prostaglandin in the plasma sample.

2. The method of claim 1 wherein the amount of the prostaglandin in the sample is correlated with prostacyclin amount in the sample.

3. The method of claim 1 wherein the plasma sample is obtained from a patient receiving intravenous prostaglandin therapy.

4. The method of claim 1 wherein concentration of said conjugate in the assay is about $1 \times 10^{-10}$ M.

5. A kit for measuring prostacyclin in plasma comprising:
   (1) an anti-6-keto-prostaglandin $F_{1\alpha}$ (6-keto-$PGF_{1\alpha}$) antibody;
   (2) an anti-immunoglobulin antibody that binds to the anti-6-keto-$PGF_{1\alpha}$-antibody; and
   (3) a conjugate comprising 6-keto-$PGF_{1\alpha}$ covalently bound to an aequorin mutant;
   wherein said aequorin mutant comprises serine substitutions for all three cysteine residues as present in wild-type aequorin (Cys→Ser), wherein said aequorin mutant further comprises a single cysteine residue substituted at amino acid position 69 (Ala69→Cys), 70 (Gly70 →Cys), 74(Gly74→Cys) or 76 (Glu76→Cys), and wherein the 6-keto-$PGF_{1\alpha}$ is coupled to the aequorin mutant via reaction with the sulfhydryl group of the single cysteine.

\* \* \* \* \*

```
SEQUENCE LISTING

<160> NUMBER OF SEQ ID NOS: 10

<210> SEQ ID NO 1
<211> LENGTH: 54
<212> TYPE: DNA
<213> ORGANISM: Artificial Sequence
<220> FEATURE:
<223> OTHER INFORMATION: Artificial sequence of unknown origin used as
      outside primers to introduce the restriction endonuclease site for
      Hind III and Sal I restriction enzymes

<400> SEQUENCE: 1
tcttcttctt cttctaagct tgtcaagctt acatcagact tcgacaaccc aaga            54

<210> SEQ ID NO 2
<211> LENGTH: 39
<212> TYPE: DNA
<213> ORGANISM: Artificial Sequence
<220> FEATURE:
<223> OTHER INFORMATION: Artificial sequence of unknown origin used as
      outside primers to introduce the restriction endonuclease site for
      Hind III and Sal I restriction enzymes

<400> SEQUENCE: 2
agaagaagaa gagtcgacca gatctggtac ccgggaatt                             39

<210> SEQ ID NO 3
<211> LENGTH: 30
<212> TYPE: DNA
<213> ORGANISM: Artificial Sequence
<220> FEATURE:
<223> OTHER INFORMATION: Artificial sequence of unknown origin used for
      PCR

<400> SEQUENCE: 3
```

```
gccttcttcg gaggatgtgg aatgaaatat                                            30
```

<210> SEQ ID NO 4
<211> LENGTH: 30
<212> TYPE: DNA
<213> ORGANISM: Artificial Sequence
<220> FEATURE:
<223> OTHER INFORMATION: Artificial sequence of unknown origin used for
      PCR

<400> SEQUENCE: 4

```
atatttcatt ccacatcctc cgaagaaggc                                            30
```

<210> SEQ ID NO 5
<211> LENGTH: 30
<212> TYPE: DNA
<213> ORGANISM: Artificial Sequence
<220> FEATURE:
<223> OTHER INFORMATION: Artificial sequence of unknown origin

<400> SEQUENCE: 5

```
gcttgcatga aatatggtgt ggaaactgat                                            30
```

<210> SEQ ID NO 6
<211> LENGTH: 30
<212> TYPE: DNA
<213> ORGANISM: Artificial Sequence
<220> FEATURE:
<223> OTHER INFORMATION: Artificial sequence of unknown origin

<400> SEQUENCE: 6

```
atcagtttcc acaccatatt tcatgcaagc                                            30
```

<210> SEQ ID NO 7
<211> LENGTH: 30
<212> TYPE: DNA
<213> ORGANISM: Artificial Sequence
<220> FEATURE:
<223> OTHER INFORMATION: Artificial sequence of unknown origin

<400> SEQUENCE: 7

```
gctggaatga aatattgtgt ggaaactgat                                            30
```

<210> SEQ ID NO 8
<211> LENGTH: 30
<212> TYPE: DNA
<213> ORGANISM: Artificial Sequence
<220> FEATURE:
<223> OTHER INFORMATION: Artificial sequence of unknown origin

<400> SEQUENCE: 8

```
atcagtttcc acacaatatt tcattccagc                                            30
```

<210> SEQ ID NO 9
<211> LENGTH: 30
<212> TYPE: DNA
<213> ORGANISM: Artificial Sequence
<220> FEATURE:
<223> OTHER INFORMATION: Artificial sequence of unknown origin

<400> SEQUENCE: 9

```
atgaaatatg gtgtgtgcac tgattggcct                                            30
```

<210> SEQ ID NO 10
<211> LENGTH: 30
<212> TYPE: DNA

-continued

```
<213> ORGANISM: Artificial Sequence
<220> FEATURE:
<223> OTHER INFORMATION: Artificial sequence of unknown origin

<400> SEQUENCE: 10
aggccaatca gtgcacacac catatttcat                                      30
```